United States Patent
Muehlsteff (10) Patent No.: US 9,883,821 B2
(45) Date of Patent: Feb. 6, 2018

(54) METHOD AND APPARATUS FOR MONITORING THE RESPIRATION ACTIVITY OF A SUBJECT

(75) Inventor: Jens Muehlsteff, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 221 days.

(21) Appl. No.: 13/820,172

(22) PCT Filed: Sep. 19, 2011

(86) PCT No.: PCT/IB2011/054085
§ 371 (c)(1),
(2), (4) Date: Mar. 1, 2013

(87) PCT Pub. No.: WO2012/038877
PCT Pub. Date: Mar. 29, 2012

(65) Prior Publication Data
US 2013/0172770 A1    Jul. 4, 2013

(30) Foreign Application Priority Data
Sep. 22, 2010 (EP) .................................. 10178208

(51) Int. Cl.
*A61B 5/113* (2006.01)
*A61B 5/05* (2006.01)
(Continued)

(52) U.S. Cl.
CPC .......... *A61B 5/1135* (2013.01); *A61B 5/0507* (2013.01); *A61B 5/18* (2013.01);
(Continued)

(58) Field of Classification Search
CPC .... A61B 5/1135; A61B 5/6891; A61B 5/0205
See application file for complete search history.

(56) References Cited

U.S. PATENT DOCUMENTS

| 2010/0152600 A1* | 6/2010 | Droitcour et al. ............ 600/534 |
| 2014/0163343 A1 | 6/2014 | Heneghan et al. |

FOREIGN PATENT DOCUMENTS

| JP | 01115344 A | 5/1989 |
| JP | 2009538720 A | 11/2009 |

OTHER PUBLICATIONS

Muehlsteff: "Comparison of Respiration Rate Monitoring With a Low-Cost Doppler-Radar Sensor and Inductive Thorax-Plethysmography"; World Congress on Medical Physics and Biomedical Engineering, Sep. 2009, Diagnostic and Therapeutic Instrumentation, Clinical Engineering, Olaf Dossel, Wolfgang C. Schlegel, Springer, vol. 25/7, pp. 768-771.

* cited by examiner

*Primary Examiner* — Catherine B Kuhlman (57) ABSTRACT

The invention relates to a method for monitoring the respiration activity of a subject, comprising the acquisition of a sensor signal of at least one Doppler-Radar sensor representing the respiration activity of a subject, the transformation of the sensor signal into a transformation signal being a series according to Formula (I) where $a_k$ is a set of predetermined constant coefficients specific for one individual subject, and processing the transformation signal S(t). The transformation signal can be analyzed with basic signal processing techniques that are applied in the field of inductive plethysmography. The invention is further related to a corresponding monitoring system.

25 Claims, 4 Drawing Sheets

(51) Int. Cl.
*A61B 5/18* (2006.01)
*A61B 5/00* (2006.01)
*A61M 21/02* (2006.01)
*G01S 13/62* (2006.01)
*G01S 13/88* (2006.01)
*G06K 9/00* (2006.01)

(52) U.S. Cl.
CPC ............ *A61B 5/486* (2013.01); *A61B 5/4836* (2013.01); *A61B 5/6891* (2013.01); *A61B 5/7225* (2013.01); *A61B 5/7278* (2013.01); *A61M 21/02* (2013.01); *G01S 13/62* (2013.01); *G01S 13/88* (2013.01); *G06K 9/00845* (2013.01)

METHOD AND APPARATUS FOR MONITORING THE RESPIRATION ACTIVITY OF A SUBJECT

FIELD OF THE INVENTION

The invention relates to the field of monitoring the respiration activity of a subject, for example, in clinical applications, systems for monitoring the physiological state of a driver or passenger in a vehicle, a biofeedback system for controlling the subject's relaxation, or the like.

BACKGROUND OF THE INVENTION

Monitoring systems for measuring the respiration activity of a subject are known for various applications. For example, in clinical intensive care situations, such applications are used to monitor the respiration activity of a patient. Another application is a biofeedback system based on guided breathing exercises to assist a subject to fall asleep. Moreover, a further application for a method and a device for monitoring the respiration activity is the early detection of the drowsiness of a driver of a vehicle. In all these applications sensors are used to acquire a sensor signal representing the respiration activity of the subject of interest, and this signal is further processed and interpreted by the system.

A measuring principle to monitor the respiration effort is thorax inductive plethysmography, where a band is placed around the subject's thorax and monitors the change of the cross sectional area of the thorax due to breathing. Although such a so-called respiband is commonly used in medical applications, however, it is not acceptable in consumer product applications, like the above mentioned biofeedback systems or driver monitoring systems, since the attachment of the band is inconvenient, cumbersome and not acceptable for the common user. For this reason contactless methods are preferred. Sensor based monitoring systems exist that comprise an array of contactless sensors such as radar sensors based on the Doppler-Radar principle. Each of these sensors is able to detect a change of a distance during a time period of an object from the sensor. Due to their operational principle Doppler-Radar sensors can be used for detecting a breathing related thorax motion. They can readily be integrated into furniture parts or in car equipment such as a car seat or the steering wheel. For example, for the above mentioned application of early detection of a driver's drowsiness, an array of Doppler-Radar sensors can be integrated into the backrest of the drivers seat. By such an array a contactless reliable monitoring of the breathing activity is possible.

In the use of the well-known method of inductive plethysmography, as mentioned above, the signal processing can be performed on the basis of a vast experience, however, the method of contactless monitoring the respiration activity with the help of Doppler-Radar sensors is more difficult because of a lack of such experience. An important problem in this context is that the algorithms developed for respiband measurements cannot be readily transferred to Doppler-Radar sensor measurements and still have to be developed to provide processing results with the same reliability. Generally there is a desire to apply the experiences with well-known measurement techniques, like inductive or resistive measuring, to the field of Doppler-Radar measurements.

SUMMARY OF THE INVENTION

It is therefore an object of the present invention to provide a method for monitoring the respiration activity of a subject with the help von Doppler-Radar sensors wherein basic signal processing techniques can be used that have already been tested in the field of inductive plethysmography, to simplify the development of a respective contactless monitoring system and to provide processing results with higher reliability.

Another object of the present invention is to provide a respective apparatus for monitoring the respiration activity of a subject that operates according to the above mentioned principles.

This objects are achieved by a method for monitoring the respiration activity of the subject according to claim 1, as well as by an apparatus according to claim 9.

According to the method according to the present invention, a sensor signal $D(t)$ of at least one Doppler-Radar sensor is acquired that represents the respiration activity of a subject. According to the well-known Doppler principle electro magnetic waves are reflected at the chest wall and undergo a Doppler frequency shift if the chest wall is moving due to the respiration of the subject. Therefore the received signal contains information of the thorax motion.

This sensor signal $D(t)$ is transformed into a so-called transformation signal $S(t)$, $S(t)$ being a series according to $$S(t) = \sum_{k=0}^{m} a_k D(t)^k \qquad (1)$$

that is, the transformation signal $S(t)$ represents the sum of terms each representing powers of the original sensor signal $D(t)$, multiplied by a constant coefficient $a_k$. One set of $a_k$, $k=0$ to m can be determined for a suitably chosen number m. The resulting transformation signal $S(t)$ can then be further processed.

By the above mentioned equation (1), the original sensor signal $D(t)$ is transformed into a transformation signal $S(t)$ that represents an estimation of a corresponding inductive plethysmographic signal measured at the same subject under the same conditions. However, the transformation signal $S(t)$ provides the advantage that it can be treated with well-known signal processing methods, especially with the same algorithms as in measuring an inductive plethysmographic signal originally by a respiband, without the use of Doppler-Radar sensors.

The mathematical relation between the Doppler-Radar signal $D(t)$ and the an estimated plethysmographic signal $S(t)$ according to equation (1) is based on the following derivation.

The human thorax can be described by an artificial torso model, where the radius of the thorax, which is assumed to be cylindrical, changes due to breathing homogeneously for all directions. The signal $S(t)$ of an associated respiband that extends around the circumference of the thorax can than be expressed by $$S(t) = \alpha L (R_0 + \Delta R(t))^2 = \alpha L (R_0^2 + 2R_0 \Delta R(t) + \Delta R(t)^2) \qquad (2)$$

In this equation (2) $R(t)$ is the radius of the thorax, that is separated in a reference radius $R_0$ and a time varying term $\Delta R(t)$. Here, the length L is assumed to be constant.

On the other hand, a Doppler-Radar signal acquired by a Doppler-Radar sensor is proportional to the distance $\Delta R(t)$ between the sensor and the subject only, according to the following equation (3):

$$D(t) = \beta \Delta R(t) \qquad (3)$$

In order to transform the radar based measured signal D(t) to S(t), D(t) according to the above equation (3) is inserted into equation (2), which gives:

$$S(t) = \alpha L R_0 + \frac{2\alpha L R_0}{\beta} D(t) + \frac{\alpha L}{\beta^2} D(t)^2 \qquad (4)$$

This expression can be written as a sum of three terms:

$$S(t) = a_0 + a_1 D(t) + a_3 D(t)^2 \qquad (5)$$

Since a human torso has usually not a cylindrical shape, the above expression (5) can be generalized as follows:

$$S(t) = \sum_{k=0}^{m} a_k D(t)^k \qquad (1)$$

That is, above equation (1) represents a generalization of the simplified torso model that has been assumed in the above considerations.

$a_k$ is a set of predetermined constant coefficients that may be specific for a individual subject. Such a set of $a_k$ can be acquired in a calibration procedure in which a plethysmographic signal and a Doppler-Radar sensor signal are measured at the same time, and a set of $a_k$ is derived from this measurement. The number m can be chosen arbitrarily.

Once a set of $a_k$ is determined for a subject to be monitored, an estimated transformation signal S(t) can be determined by being transformed from the Doppler-Radar sensor signal D(t) and further processed according to the signal processing methods applicable to inductive plethysmographic signals. With other words, the estimated transformation signal S(t) is treated like an original respiration signal acquired with a respiband.

According to a preferred embodiment of the present invention, the set of coefficient $a_k$ is taken from a look-up table.

In this case the set of coefficient $a_k$ is present when the measurement begins and can be taken, for example, from a suitable storage unit to transform the measured sensor signal D(t) to the transformation signal S(t), that can be further processed.

According to another preferred embodiment, this look-up table contains a plurality of different sets of coefficients $a_k$.

To use a set $a_k$ that is specific for an individual subject, each set of $a_k$ has to be selected from a plurality of sets $a_k$ to choose the one that matches the present subject to be monitored.

Preferably this subject is identified, and a corresponding sets of coefficients $a_k$ is chosen from the plurality of sets of coefficients $a_k$ according to the result of the identification. This identification can take place automatically by the monitoring system, or the user is requested to input an identification information into the system. According to this information, a set of $a_k$ is selected from the look-up table. Alternatively a default set of $a_k$ can be chosen for the further processing in case the result of the identification is negative, that is, if no matching set of $a_k$ can be found.

According to another preferred embodiment of the invention, a set of coefficients $a_k$ for an individual subject is acquired in a calibration step, comprising measuring a plethysmographic signal S'(t) related to the subject's breathing over a period of time; measuring a sensor signal D(t) related to the subject's thorax motion over the same period of time; and determine a set of coefficients $a_k$ from S'(t) and D(t) according to the relation $$S'(t) = \sum_{k=0}^{m} a_k D(t)^k. \qquad (6)$$

This calibration process can be done, for example, in a garage or at the site of the car seller. The determination of the coefficients $a_k$ can be done via standard signal processing schemes of data from simultaneous measurements with a respiband and the radar set up.

According to a preferred embodiment of the present invention, D(t) is the sum of the sensor signals $D_i(t)$, i=1 to n, from n sensors.

In the presence of more than one Doppler-Radar sensor, all sensor signals $D_i(t)$ are summarized to a common sensor signal D(t) that is further processed according equation (1), that is, it is further transformed into the transformation signal S(t). In this case one set of constant coefficients $a_k$ is necessary for an individual subject.

Forming the sum D(t) of all Doppler-Radar sensors provides the advantage that possible irregularities in the respiration of the subject can be perceived by the monitoring system easier than in the case of using only one Doppler-Radar sensor. Typically a plurality of sensors is distributed in a measurement range that represents an area covering the moving part of the thorax during the breathing activity. In a simplified example, the chest movement and the abdominal movements are measured by different sensors. While a irregularity like, for example, yawning is measured only by one sensor, this irregularity may be missed by the other sensor. If, however, both sensor signals are summed up, the irregularity will still show in the sum signal. With a help of a pattern detection algorithm, irregularities in the breathing process can be found in the sum signal.

According to another preferred embodiment of the present invention, a plurality of sensor signals $D_i(t)$, i=1 to n is acquired from a plurality of n sensors, and one set of coefficients $a_k$ is determined for each one of these sensors.

In this case the transformation signal can be determined individually for each sensor signal $D_i(t)$ with the help of a respective set of coefficients $a_{ki}$, so that an estimated transformation signal $S_i(t)$ will exist corresponding to each sensor signal $D_i(t)$. The set of coefficients $a_{ki}$ for each sensor must be determined individually in the calibration procedure as described above.

Preferably a transformation signal $S_i(t)$ is derived for each sensor i according to $$S_i(t) = \sum_{k=0}^{m} a_{ki} D_i(t)^k \qquad (7)$$

and a summarized transformation signal $\hat{S}(t)$ is calculated as the sum $$\hat{S}(t) = \sum_{i=1}^{n} S_i(t) \qquad (8)$$

of the transformation signals $S_i(t)$ of the sensors.

This means that the sum of the transformation signals is formed from the individual transformation signals $S_i(t)$ derived from each original Doppler-Radar sensor signal $D_i(t)$.

A corresponding system for monitoring the respiration activity of a subject according to the present invention comprises at least one Doppler-Radar sensor provided to acquire a sensor signal D(t) representing the respiration activity of a subject, a sensor transformation unit provided for transforming the sensor signal D(t) into a transformation signal S(t), S(t) being a series according to $$S(t) = \sum_{k=0}^{m} a_k D(t)^k \quad (1)$$

where $a_k$ is a set of predetermined constant coefficients, a storage unit for storing sets of $a_k$ of predetermined constant coefficients, and a processing unit for processing the transformation signal S(t).

Preferably this system further comprises a plurality of Doppler-Radar sensors disposed at different positions within a measurement range.

This measurement range typically corresponds to an area of the thorax moving during the breathing motion. For example, one sensor can be provided in the chest region, while the other sensor is disposed in the abdominal region so that each sensor measures different movements during the breathing motion. This increases the chance to measure a breathing irregularity that may only concern the movement in one thorax region, while another region shows a normal breathing activity.

According to another preferred embodiment of this system, the sensor transformation unit is provided for transforming a sensor signal $D_i(t)$ of each sensor i into a transformation signal $S_i(t)$ and to summarize the resulting transformation signals $S_i(t)$ to a summarized transformation signal $\hat{S}(t)$.

According to another preferred embodiment, the sensor transformation unit is provided for summarizing sensor signals $D_i(t)$ of the sensors to a sum D(t) and to transform the summarized signal D(t) into a transformation signal S(t). This transformation can be performed according to the rules according to the present invention as already described, i.e. to transform the summarized signal D(t) into a power series according to equation (1) so that the sum of these terms is represent by the transformation signal S(t).

BRIEF DESCRIPTION OF THE DRAWINGS

These and other aspects of the invention will be apparent from and elucidated with reference to the embodiments described hereinafter. In the drawings.

DETAILED DESCRIPTION OF EMBODIMENTS

Figure 1:
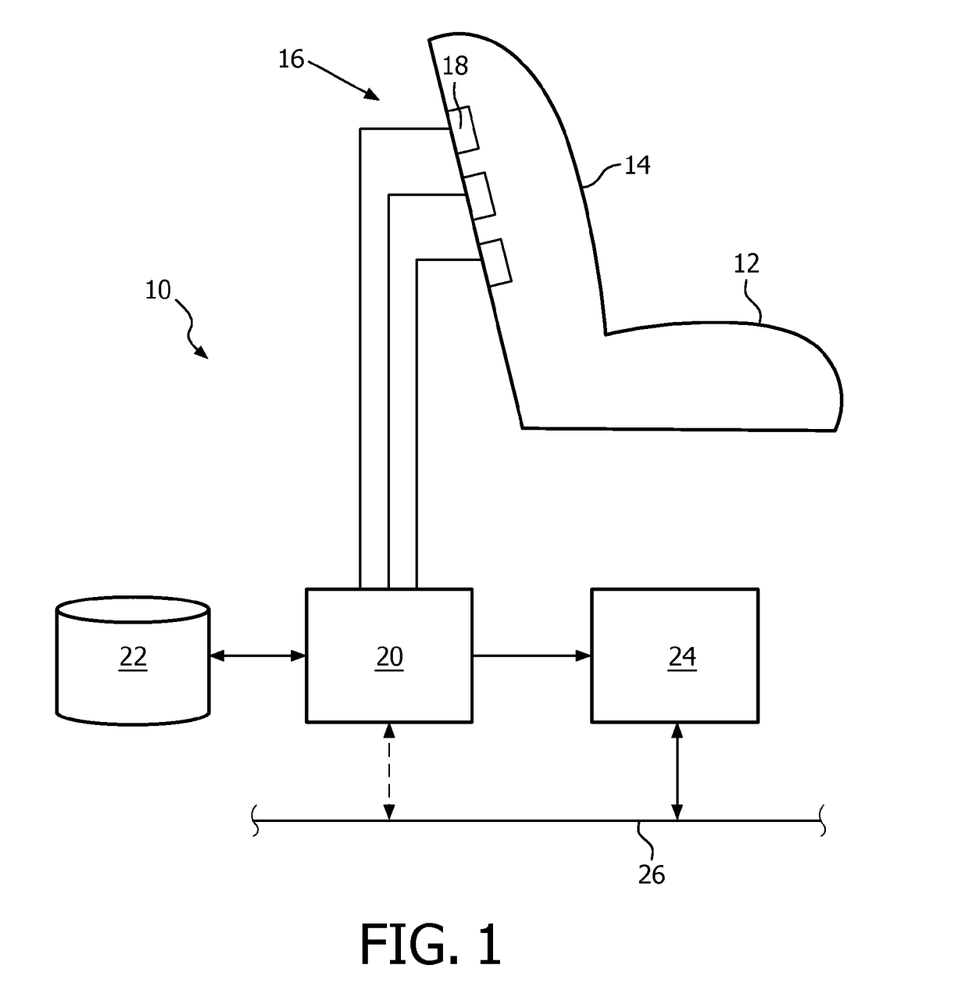
FIG. 1 is a schematic view of a sensor based monitoring system according to a first embodiment of the present invention.

FIG. 1 shows a system 10 for monitoring the respiration activity of a subject, for instance a driver located on a driver's seat 12 of a vehicle. Alternatively the seat or chair is part of a biofeedback system for monitoring or controlling the relaxation of the person using the seat. Instead of a seat or chair the system may comprise a mattress. Such an embodiment is described more in detail below in connection with FIG. 4. At the rear side of the back rest 14 of the seat 12, an array 16 of sensors 18 is integrated into the seat 12. These sensors are Doppler-Radar sensors to monitor the breathing activity of the subject. Each sensor 18 has a defined measuring range corresponding to a determined area of the subject's thorax. For example, an upper sensor 18 of the array 16 can be provided to monitor the chest area of the subject, while a lower sensor 18 is provided to monitor the abdominal movements of the thorax. According to the Doppler principle, electromagnetic waves emitted by the sensors 18 are reflected at the chest wall and undergo Doppler frequency shift if the chest wall is moving due to the respiration of the subject. Therefore the signals received by the sensors 18 contain information about the thorax motion.

The system 10 further comprises a sensor transformation unit 20 to receive sensor signals acquired by the Doppler-Radar sensors 18. This unit 20 may further comprise control functions for controlling the sensors 18, for example, to activate only a limited subset of sensors 18 within the array 16. That is, the transformation unit 20 is not only provided for signal transformation tasks, as will be laid out in the following, but may comprise further functions.

Once the signal transformation unit 20 has received a sensor signal D(t) of the sensors 18, this sensor signal D(t) is transformed into a transformation signal S(t), as will be further explained below. The transformation is such that the resulting transformation signal S(t) can be handled like a signal resulting from an inductive plethysmography, i.e. a respiband measurement that measures the change of the circumference of the thorax during the breathing motion. Existing signal processing methods can be applied readily to such a transformated signal S(t), which is treated as an estimated plethysmographic signal.

Sets of coefficients $a_k$ necessary for this transformation are stored in a storage unit 22 that communicates with the signal transformation unit 20. Each set of predetermined constant coefficients $a_k$ may be specific for an individual subject. For different subjects a plurality of sets of coefficients $a_k$ is stored in the storage unit 22.

Once the transformation signal S(t) has been determined, it can be further processed in a processing unit 24 to analyze the transformation signal in view of irregularities. Such an irregularity could be yawning of the subject, which explicitly shows in a pattern of at least one sensor signal of one of the sensors 18. If such an irregularity is identified, this is taken as an indication of relaxation of the person in the seat. In case the seat is the seat of a driver of a vehicle the yawning may be considered as an indication of a critical state of the driver concerned, and a feedback signal could be given to him. Similarly in case the seat is a part of a biofeedback system intended for assisting the user to relax a feedback signal can be given to the use. In case of the seat is a driver's seat, The signal indicating a certain irregularity (assumed to represent respective certain physiological state of the subject) could be output by the processing unit 24 and transmitted via a bus system. In case the of a vehicle this could be for instance the CAN bus 26 of the car. In other applications the seat or chair may be connected to a local area network (wired or wireless). Via the bus-system or network the processing unit would be connected to other hardware units, that may arranged to produce a feedback signal to the user. This signal could for in stance be an audio and/or video signal.

It is noted that the example of the monitoring system 10 in FIG. 1 is only one application of monitoring the respiration activity of a subject. Moreover, the schematic architecture of the system 10 comprising a signal transformation unit 20 and a processing unit 24 is only to be understood as an example. The transformation function and the further processing functions could also be performed by one single hardware unit, and so the division of these tasks into two operational units 20 and 24 has only been made for explanatory reasons. Just to mention one further example, the different units 22, 24 and 26 could be connected via the bus system or network 26 itself.

Figure 2:
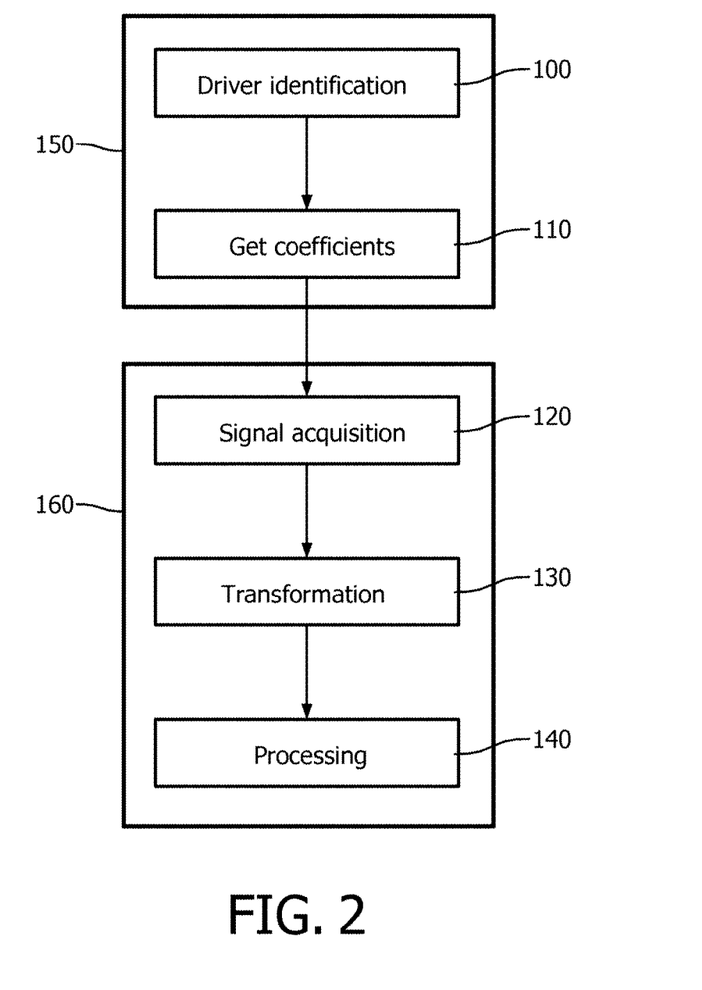
FIG. 2 is a flow diagram showing an embodiment of the method according to the present invention.

An embodiment of a method for monitoring the respiration activity of a subject with the help of the monitoring system 10 in FIG. 1 will be explained in the following with regard to the flow diagram of FIG. 2.

First, in step 100, the user is identified as the subject to be monitored. This identification can be performed automatically by the system by detecting certain characteristics of the subject, or by input of a user ID into the system 10. Once the driver (subject) is identified, one set of coefficients $a_k$ is polled from the storage unit 22 according to result of the identification (step 110). Usually a plurality of sets of constants $a_k$ is stored within a look-up table inside the storage unit 22, and one of these sets $a_k$ is selected according to the identification result.

If no identification of the subject is possible, i.e. the result of the identification step 100 is negative and no set of individual $a_k$ matching the subject is present in the look-up table, a default (standard) set of $a_k$ can polled from the look-up table and the further processing can be carried out on this basis.

The further meaning of this set of coefficients $a_k$ necessary for a single transformation will be explained below.

In a further step 120, sensor signals D(t) are acquired from the sensors 18 representing the respiration activity of the subject. The sensor signal D(t) of a Doppler-Radar sensor is proportional to the distance between the sensor and the subject (i.e. the thorax wall at which the electromagnetic waves are reflected back to the sensor). To simplify the further processing of the sensor signals, the original sensor signal is transformed into a transformation signal S(t) in a transformation step 130 according to the following equation:

$$S(t) = \sum_{k=0}^{m} a_k D(t)^k \tag{1}$$

This means that the transformation signal S(t) is formed by a sum of terms, each term being a power of the original sensor signal D(t) multiplied with a coefficients $a_k$. The number m can be chosen as desired. $a_k$, k=0 to m represent the coefficients that are taken from the look-up table in the foregoing step 110.

This transformation signal S(t) represents an estimated plethysmographic signal that can be treated as a signal acquired from a respiband or the like. Signal processing methods applicable to such respiband signals can be used for further processing the transformation signal S(t) in a processing step 140. It is, however, noted that the transformation signal S(t) can also be treated with signal processing methods applicable to resistive measurements, since the signals acquired by these methods can also be developed mathematically to a power series.

While the user identification step 100 and the subsequent step 110 of polling the coefficients from the look-up table represent an initialization procedure 150 of the whole process, it is understood that the following steps 120, 130 and 140 will be carried out (and repeated) continuously in a permanent monitoring routine 160. That is to say, during monitoring the subject, there will be a permanent process of signal acquisition, immediate transformation of the acquired signals and eventually further processing of the transformation signal.

In the case of a plurality of sensors 18 as shown in FIG. 1, there are different possibilities to handle the original sensor signals D(t). One possibility is to sum up the sensor signals $D_i(t)$, i=1 to n from n sensors and to further process the sum D(t) in the way as described above. This means that the sum of all sensor signals $D_i(t)$ is treated like one common sensor signal D(t). For the further transformation into the transformation signal S(t) only one set of coefficients $a_k$ is necessary for one subject.

Using a plurality of sensors 18 provides the advantage that each of these sensors 18 can be disposed at a different position within the array 16. For example, an irregularity in the breathing rhythm can be detected by one sensor 18 while another sensor 18 does not detect any irregularities. However, in the sum D(t) of both of these sensor signals $D_i(t)$, the irregularity will be present. One typical example for an irregularity is a yawning pattern that may show in the sensor signals of one sensor but is not detectable in the sensor signals of another sensor.

Another possibility to handle the sensor signals $D_i(t)$, i=1 to n of n sensors is to transform each sensor signal $D_i(t)$ into a corresponding transformation signal $S_i(t)$, i=1 to N, so that N transformation signals $S_i(t)$ will be present. Each of these transformation signals $S_i(t)$ is calculated according to $$S_i(t) = \sum_{k=0}^{m} a_{ki} D_i(t)^k. \tag{7}$$

It is clear that one set of coefficients $a_k$, is necessary in this case for each sensor.

The different transformation signals $S_i(t)$ (gained in the transformation step 130) are summarized in the following to calculate a sum $$\hat{S}(t) = \sum_{i=1}^{n} S_i(t) \tag{8}$$

of the transformation signals $S_i(t)$ of the sensors. This summarized transformation signal $\hat{S}(t)$ can then be further processed (step 140) and treated as an estimated plethysmographic signal with the according signal processing algorithms.

Figure 3:
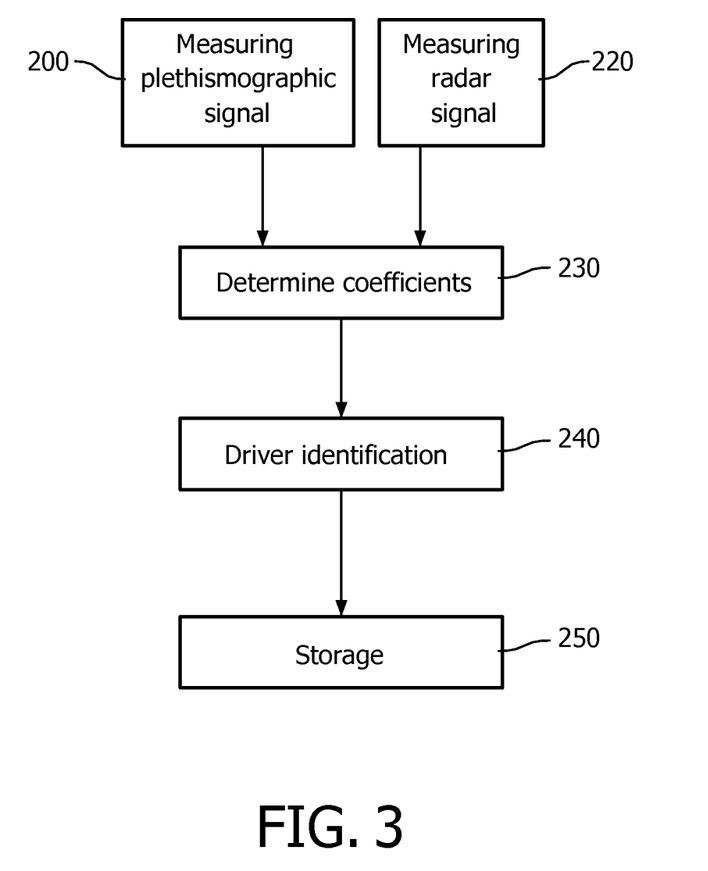
FIG. 3 is another flow diagram demonstrating a calibrating step according to the method of the present invention.

To acquire sets of predetermined constant coefficients $a_k$, a calibration step can be performed that is shown in the flow diagram of FIG. 3.

In this calibration step, a plethysmographic signal S'(t) is measured over certain period of time. Such a signal S'(t) can be taken by a respiband measurement and is related to the subject's thorax volume (step 200). At the same time, a Doppler-Radar sensor signal D(t) related to the subject's thorax motion is measured (step 220). From both measurements, coefficients $a_k$ are calculated according to the relation $$S'(t) = \sum_{k=0}^{m} a_k D(t)^k. \quad (6)$$

in a following step 230 based on state-of-the-art statistical methods.

The user may be requested to input a user ID (step 240), and the set of coefficients $a_k$ is stored within the look-up table together with user identification data (step 250).

According to the chosen set up, the coefficients $a_k$ can be determined for each sensor 18 so that in the calibration step, coefficients $a_k$ are determined for the whole set of sensors and stored together with the user ID. In case of use in a vehicle this could be stored in the car management system. In case the system is used for instance in a home as a relaxation system, as described below more in detail in connection with FIG. 4, it could be stored locally or at another module or computer connected to a home network. It is possible to communicate all data, including the sets of coefficients $a_k$ and user identification data, via the bus or network 26, as shown in FIG. 1.

Although the invention has been described above to create a transformation signal that corresponds to an estimation of a signal gained by inductive plethysmography with the help of a respiband, it is, however, possible to interpret the transformation signal as an estimated signal acquired by other methods. For example, resistive measuring of the circumference of the subject's thorax can also be estimated by the transformation signal, since a resistive measurement signal can also be simulated by a series of terms that include the Doppler radar signal information. In this respect other measurement techniques can possibly be acknowledged.

Figure 4:
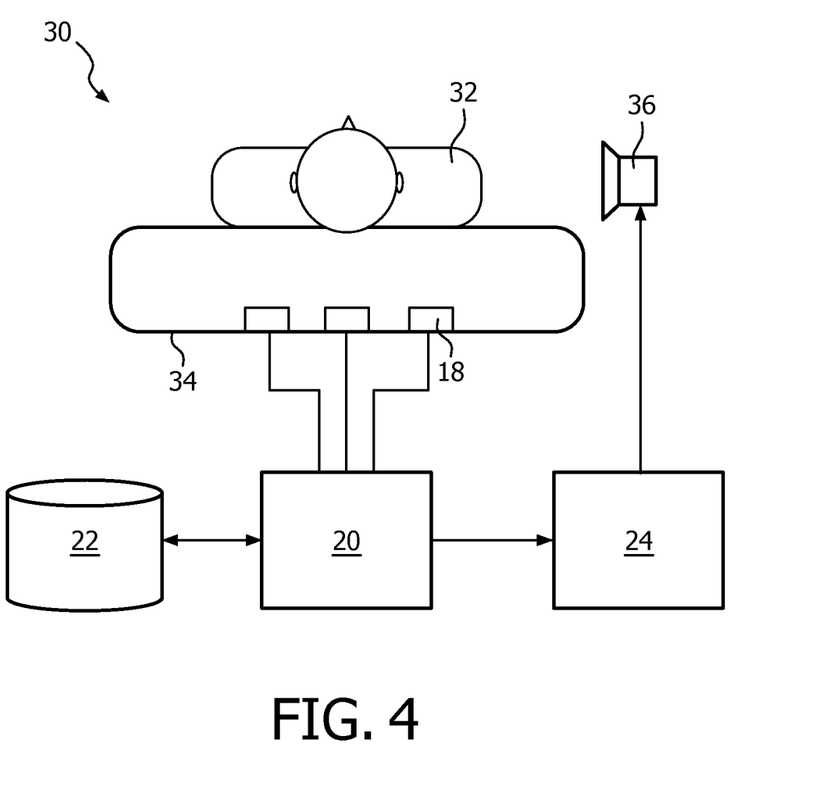
FIG. 4 is a schematic view of another sensor based monitoring system according to a second embodiment of the present invention

FIG. 4 shows another embodiment of a system 30 for monitoring the respiration activity of a subject 32 according to the present invention. This system 30 comprises a mattress wherein the array of sensors 18 is integrated to monitor a subject 32 lying on the top surface of the mattress 34. The system 30 further comprises a signal transformation unit 20 and a processing unit 24, as well as a storage unit 22. The operation principle of the sensors 18, the signal transformation unit 20, the processing unit 24 and the storage unit 22 is basically the same as explained with respect to FIG. 1, so that further explanations are omitted here for the sake of brevity. In the embodiment of FIG. 4, the processing unit 24 communicates with an output unit 36 to generate an audio and/or video feedback signal perceivable by the subject 32 in case a respective command is received from the processing unit 24. Such a feedback system can assist the subject 32 to relax by pacing the respiration rhythm, i.e. to give a perceivable feedback on the respiration as presently measured. Moreover, a similar system 30 comprising sensors 18 integrated in a mattress 34 can be used in clinical care for monitoring a patient.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A processing system for monitoring the respiration activity of a subject, the processing system comprising:
an input configured to receive multiple sensor signals Di(t) associated with multiple Doppler-Radar sensors measuring the respiration activity of a subject,
a sensor signal transformer configured to transform the sensor signals Di(t) into a transformed digital signal S(t), S(t) being a series according to:

$$S(t) = \sum_{k=0}^{m} a_k D(t)^k,$$

where $a_k$ is a set of predetermined constant coefficients, and
a processor configured to:
determine from the transformed digital signal S(t) a level of respiration activity of the subject;
determine whether an irregularity in the level of respiration activity exists, wherein the irregularity represents a pattern in the sensor signals of at least one sensor, not detected in sensor signals associated with other sensors; and
generate a feedback signal dependent on the transformed digital signal, when an irregularity in the level of respiration activity is determined, the feedback signal being provided to the subject for pacing their respiration activity by providing perceivable information to assist the subject in controlling the respiration activity.

2. A system for monitoring respiration activity of a subject, the system comprising:
multiple Doppler-Radar sensors configured to provide sensor signals Di(t) associated with multiple Doppler-Radar sensors and representing the respiration activity of a subject,
a signal transformer communicating with the Doppler-Radar sensors, and configured to transform the sensor signals Di(t) into a transformed signal S(t), S(t) being a series according to:

$$S(t) = \sum_{k=0}^{m} a_k D(t)^k,$$

where $a_k$ is a set of predetermined constant coefficients;
a memory store configured to store sets $a_k$ of predetermined constant coefficients; and
a processing unit communicating with the transformer and configured to process the transformed signal S(t) to:
determine a level of respiration activity of the subject based on the transformed signal;
determine an irregularity in the level of respiration activity based on the transformed signal and the level of respiration activity of the subject, wherein the irregularity represents a pattern in the sensor signal of a sensor not detected in sensor signals associated with other sensors; and generate a feedback signal based on the transformed signal, provided to the subject, when an irregularity in the level of respiration activity is determined, the feedback signal pacing the respiration activity by providing a perceivable indication to assist the subject in controlling their respiration activity.

3. The system according to claim 2, wherein the Doppler RADAR sensors are configured to be positioned relatively apart within a measurement range of the subject.

4. The system according to claim 3, wherein the signal transformation unit is provided for:
  transforming a sensor signal $D_i(t)$ of each sensor i into a transformation signal $S_i(t)$; and
  summarizing the resulting transformation signals $S_i(t)$ to a summarized transformation signal $\hat{S}(t)$.

5. The system according to claim 3, wherein the signal transformation unit is provided for:
  summarizing sensor signals $D_i(t)$ of the sensors to a sum signal $D(t)$; and
  transforming the sum signal $D(t)$ into a transformation signal $S(t)$.

6. A monitoring control system comprising:
  a plurality of Doppler Radar sensors positioned in an array, each of the sensors configured to be associated with a region of a user;
  a processor configured to:
    receive signals via an input, from the plurality of Doppler Radar sensors, the input configured to receive the signals of the Doppler Radar sensors;
    for a received signal of the received signals, represent the received signal in a digital signal form as a sum of terms each representing powers of the received signal multiplied by a set of coefficients $a_k$;
    determine a level of activity based on the represented received signal;
    determine whether an irregularity in the represented received signal is present, wherein the irregularity represents a pattern in the sensor signal of at least one sensor not detected in sensor signals associated with other sensors; and
    generate a perceivable feedback signal based on the received signals, provided to the user after determining that the irregularity is present in the received signal, the feedback signal pacing the respiration activity by providing perceivable information assistance to the user to enter a relaxed state.

7. The monitoring control system of claim 6 comprising an input unit, the input unit providing an identification of the user.

8. The monitoring control system of claim 6, the processor configured to automatically determine an identification of the user.

9. The monitoring control system of claim 6, wherein representing the received signal in a digital form comprises transforming the received sensor signal, $D(t)$, into a transformation signal $S(t)$, according to $$S(t) = \sum_{k=0}^{m} a_k D(t)^k,$$

where $a_k$ is a set of associated coefficients.

10. The monitoring control system of claim 9, comprising a storage unit, storing at least one set of the coefficients, $a_k$.

11. The monitoring control system of claim 10, wherein a set of the at least one set of coefficients $a_k$ is selected from the storage unit based on an identity of the user.

12. The monitoring control system of claim 10, wherein a default set of the at least one set of coefficients $a_k$ is selected from the storage unit based on an identity of the user being unknown.

13. The monitoring control system of claim 9, wherein $D(t)$ represents a sum of signals from at least one of the plurality of sensors according to:

$$D(t) = \sum_{i=1}^{n} D_i(t)$$

wherein n=the number of sensors.

14. The monitoring control system of claim 9, wherein $S(t)$ represents a sum of representations of corresponding signals from at least one of the plurality of sensors according to:

$$S(t) = \sum_{i=1}^{n} S_i(t) = \sum_{i=1}^{n} \sum_{k=0}^{m} a_k D_i(t)^k.$$

15. The monitoring control system of claim 6 comprising one of: an audio device, a visual device, and a combination thereof.

16. The monitoring control system of claim 15, wherein the feedback signal is provided to at least one of the audio device and the visual device.

17. A monitoring system comprising:
  a chair; and
  a monitoring system incorporated into a back of the chair, the monitoring system comprising:
    a plurality of Doppler Radar sensors positioned in an array within the back of the chair, each of the sensors configured to be associated with a region of a user;
    a processor configured to:
      receive multiple signals from the plurality of Doppler Radar sensors;
      represent a received signal of the multiple received signals, in a digital form as a sum of terms each representing powers of the received signal multiplied by a coefficient of a set of associated coefficients $a_k$;
      determine a level of activity of the user based on the represented received signals;
      determine whether an irregularity in the level of activity is present, wherein the irregularity represents a pattern in the sensor signal of at least one sensor, not detected in sensor signals associated with other sensors of the plurality of Doppler Radar sensors; and
      generating a perceivable feedback signal depending on the represented signal, when the presence of the irregularity is determined, the feedback signal pacing the respiration rhythm by providing the subject with a perceivable indication of the feedback signal to give them feedback on the respiration as measured.

18. The monitoring system of claim 17 comprising an input unit providing an identification of the user.

19. The monitoring system of claim 17, the processor configured to automatically determine an identification of the user.

20. The monitoring system of claim 17, comprising a storage unit storing information associated with the user.

21. The monitoring system of claim 17, comprising one of: an audio device, a visual device, and a combination thereof, wherein the feedback signal is provided to at least one of the audio device and the visual device.

22. The monitoring system of claim 17, wherein representing the received signal in a digital form comprises:
transforming the received signal, D(t), into a transformation signal S(t), according to $$S(t) = \sum_{k=0}^{m} a_k D(t)^k,$$

where $a_k$ is a set of associated coefficients.

23. The monitoring system of claim 22, wherein the set of associated coefficients is associated with an identity of the user.

24. The monitoring system of claim 22, wherein the set of associated coefficients is a default set of coefficients when the identity of the user is unknown.

25. A tangible computer-readable storage medium, which is not a transitory propagating signal or wave, configured with instructions to control a processing system for controlling the operation of a system for monitoring the respiration activity of a subject, the instructions when executed causing the system for monitoring to:

in a system for monitoring the respiration activity of a subject, acquire multiple sensor signals D(t) associated with multiple Doppler-Radar sensors of the monitoring system, the Doppler-Radar sensors measuring the respiration activity of a subject, transform, via a sensor signal transformer of the processing system, the sensor signals D(t) into a transformed signal S(t), S(t) being a series according to:

$$S(t) = \sum_{k=0}^{m} a_k D(t)^k,$$

where $a_k$ is a set of predetermined constant coefficients, and determine via a processor of the processing system, a level of respiration activity of the subject;

determine via the processor, an irregularity in the level of respiration activity, wherein the irregularity represents a pattern in the sensor signal of a sensor of the multiple sensors not detected in sensor signals associated with other sensors of the multiple Doppler-Radar sensors; and generate via the processor, a feedback signal when the irregularity in the level of respiration activity is determined, the feedback signal pacing the respiration rhythm by providing the subject with a perceivable indication to give them feedback on the respiration as measured.

* * * * *